(12) United States Patent
Taskar et al.

(10) Patent No.: US 6,674,837 B1
(45) Date of Patent: Jan. 6, 2004

(54) X-RAY IMAGING SYSTEM INCORPORATING PIXELATED X-RAY SOURCE AND SYNCHRONIZED DETECTOR

(75) Inventors: Nikhil R. Taskar, Scarsdale, NY (US); Rameshwar Nath Bhargava, Ossining, NY (US); Paul J. Patt, Northborough, MA (US)

(73) Assignee: Nan Crystal Imaging Corporation, Briarcliff Manor, NY (US)

( * ) Notice: Subject to any disclaimer, the term of this patent is extended or adjusted under 35 U.S.C. 154(b) by 0 days.

(21) Appl. No.: 10/172,704

(22) Filed: Jun. 14, 2002

Related U.S. Application Data

(60) Provisional application No. 60/298,591, filed on Jun. 15, 2001.

(51) Int. Cl.[7] .............................................. H01J 35/00
(52) U.S. Cl. ........................................ 378/122; 378/92
(58) Field of Search ................................. 378/122, 92

(56) References Cited

U.S. PATENT DOCUMENTS

| | | | | | |
|---|---|---|---|---|---|
| 4,349,740 | A | * | 9/1982 | Grassmann | 378/92 |
| 5,307,396 | A | * | 4/1994 | Tsuchino | 378/146 |
| 5,729,583 | A | * | 3/1998 | Tang et al. | 378/122 |
| 5,952,665 | A | * | 9/1999 | Bhargava | 250/483.1 |

* cited by examiner

Primary Examiner—Craig E. Church
(74) Attorney, Agent, or Firm—William L. Botjer

(57) ABSTRACT

An X-ray imaging system utilizing a pixelated X-ray source and a X-ray imaging detector operated synchronously. The imaging system may be used in industrial and medical applications. The X-ray source and X-ray detector are synchronized such that a corresponding area of the X-ray detector is activated when the corresponding area of the X-ray source is emitting X-rays. Synchronized and adaptive emission and detection of the X-rays results in scatter rejection, improved image quality, and optimum exposure and dose reduction.

20 Claims, 3 Drawing Sheets

X-RAY IMAGING SYSTEM INCORPORATING PIXELATED X-RAY SOURCE AND SYNCHRONIZED DETECTOR

REFERENCE TO RELATED APPLICATIONS

This application claims the priority of U.S. Provisional patent application Ser. No. 60/298,591 filed Jun. 15, 2001, entitled "X-ray Imaging System Incorporating Pixelated Synchronized X-ray Source and Detector"

BACKGROUND AND SUMMARY OF THE INVENTION

This invention relates to X-ray imaging systems. More specifically this application relates to X-ray imaging systems utilizing a pixelated X-ray source and a X-ray detector operated synchronously. The imaging system may be used in industrial and medical applications.

X-ray imaging systems have many applications in industrial and medical fields. In the medical field X-ray imaging is often used for cancer screening. Early detection of cancer leads to earlier treatment and higher cure/success rates. A technology which provides for earlier detection of cancers, in a more dose-efficient manner, will have significant impact on cancer treatment.

Currently, nearly all medical screening and diagnosis is based on 2-D X-ray "projection imaging". A "flood" of X-ray illumination is used to either expose film, or more recently, a (coarse) array of X-ray sensitive imaging electronics. The spatial and coherence attributes of the X-ray source have not been fundamentally altered since the original inception. The underlying tissue structure determines what X-ray fluence, or uniform X-ray exposure is required for adequate imaging. This 2-D projection imaging suffers from scatter and from the superposition of many images through the tissue thickness.

One approach to mitigating scatter has been by employing an "inverted" detector topology in which a single, small area detector is "aligned" with a scanning beam. This approach did not benefit from X-ray focusing and, as a result resulted in poor system efficiency. Nevertheless, the system did uncover some of the benefits in eliminating scatter by producing cardiac images with good image quality, S/N and reduced dosage. Another system is based on "slot-scanning". This relies on a mechanical translation of a narrow X-ray sensor and the rotation of a X-ray source. While scatter rejection is improved above the current systems, it still uses flood X-ray illumination within the irradiated slot and a cumbersome CT implementation. Also because of the lack of good X-ray focusing, it has poor energy utilization from the X-ray head.

The potential resolution capabilities of X-ray imaging are hardly being exploited. The currently approved digital systems have less high-resolution information than the current film systems. Thus cancers associated with micro-calcifications are more likely to either go under or undetected, or get passed onto biopsy analysis. Both results are undesirable. Except for the two "scanned" systems mentioned above, the current systems rely on unsophisticated scatter-rejection techniques based on "passive" concepts such as geometric enlargement, or mechanical grids. While these passive scatter rejection grids do improve image quality (S/N), they do so at the expense of greatly increasing the dosage to the patient.

The present invention is directed to a high-resolution, volumetric imaging system based on active-scanning and detection of X-rays. X-rays are uniquely suited to high-resolution imaging of deep structures. However, current X-ray imaging technology, including the recently approved flat-panel detectors, are all based on a nearly "uniform" illumination of X-rays. The newer, systems based on "slot" scanning, though reducing scatter, still rely on uniform, X-ray exposure. Consequently, none of these systems are "adaptive" within the field of view.

The present invention is directed to a system architecture and component technology that fundamentally changes the current approach and will allow for adaptive exposure within a given field of view. Stereographic, and tomographic systems can be based on this technology will eliminate image degradation due to scatter. This will provide for optimum X-ray exposure conditions, improved diagnostic images, improved patient comfort and utilization and reduced patient dosage. The complete system can be implemented without moving parts and can be entirely electrically addressed. As a result, it will be less expensive than other tomographic or CT approaches. This technology will result in a higher performance, more sensitive system.

The present invention provides the following key contributions:

Active scanning through an electrically addressable array of X-ray emitters producing a narrow beam of X-rays.

High resolution, active-pixel detection based on CCD/CMOS electronics/detectors and microchannel based high-resolution scintillation technology.

Synchronized and adaptive emission and detection resulting in scatter rejection, improved image quality, and optimum exposure and dose reduction. The X-ray emitting and sensing devices are completely electronically addressable and scaleable. Alternatively, a mechanically moving aperture can be utilized in front of the X-ray detector.

The present invention provides: several times the amount of diagnostic information while reducing exposure levels, a reduction in scatter while reducing X-ray exposure, with high image resolution. The present invention can uncover low-density, low-contrast images that is currently obscured by overlapping tissue structure and can provide pixel-by-pixel automatic-exposure.

Our previous work in the design and construction of microchannel based X-ray screens for use in X-ray systems can be found in U.S. Pat. No. 5,952,665; issued Sep. 14, 1999 Entitled Composite Nanophosphor Screen for Detecting Radiation"; U.S. Pat. No. 6,300,640 issued Oct. 9, 2001 Entitled "Composite Nanophosphor Screen For Detecting Radiation Having Optically Reflective Coatings", PCT published application No. WO 99/28764; U.S. patent application Ser. No. 09/688,662 filed Oct. 16, 2000 Entitled "High Resolution High Output Microchannel Based Radiation Sensor"; U.S. patent application Ser. No. 09/385,995 filed Aug. 30, 1999 Entitled "Microchannel High Resolution X-ray Sensor Having an Integrated Photomultiplier", and U.S. patent application Ser. No. 10/073,702 filed Feb. 11, 2002 Entitled "High Resolution Tiled Microchannel Storage Phosphor Based Radiation Sensor". The disclosures of these previous US patent applications and issued patents are hereby incorporated by reference as if fully set forth herein.

BRIEF DESCRIPTION OF THE DRAWINGS

For a better understanding of the invention, reference is made to the following drawings which are to be taken in conjunction with the detailed description to follow in which.

DESCRIPTION OF THE PREFERRED EMBODIMENTS

The X-ray Emitter

X-ray tubes of most current imaging systems are based on electron bombardment of a target material. The emitted X-ray pattern is highly divergent. "Windows" in the X-ray housing determine the angular extent of emitted X-rays. The energy distribution of emitted X-rays are determined by the electron energy and the choice of target material, typically Molybdenum, or Rhenium. Filters are used to modify the energy spectrum. Aside from minor improvements in spot size and target materials, little fundamental advances have been made over the past 30 years.

Recent advances in field emission technology have opened the potential to develop an electronically addressable planar X-ray source. The current density in certain field emitter systems can now exceed 500 A/cm$^2$. This is nearly an order of magnitude higher than available in earlier field emission systems and allows a high degree of spatial correlation between an emitter and the detector. The electron emitter in field emitter display systems is composed of minute tips, of for example, carbon-based nanotubes or metal pyramids, well under a micron in tip size. The emitters were originally been developed as a planar source of electrons for flat panel displays based on phosphors. Displays based on these planar, electrically addressable pixels are called field emission displays which are slim, flat panel vacuum devices.

Figure 1:
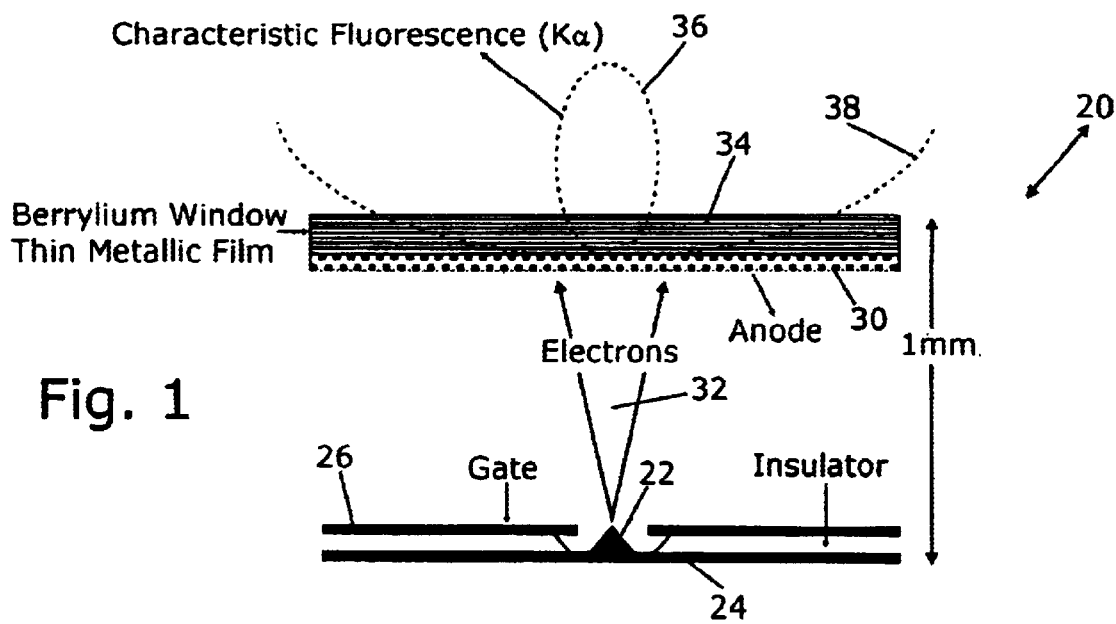
FIG. 1 is a schematic view of a field effect based X-ray emitting device used in the X-ray imaging system of the present invention.

FIG. 1 illustrates a field emission device (FED) used as a pixelated addressable X-ray source 20. X-ray source 20 includes a multiplicity of minute cathode tips 22 disposed on a substrate 24. Surrounding each tip 24 is a gate 26 separated by an insulator 28. Disposed above each tip 24 is an anode 30 formed from material such as molybdenum which emits X-rays when acted upon by an electron beam. Cathode tips 22 which can be made of silicon, carbon or molybdenum or other materials, are electron emitters under high electric field. Single tips with a radius of curvature about 100 nm have been used to generate current densities of more than 10$^8$ A/cm$^2$, and arrays of tips have generated current densities of 10 to 2400 A/cm$^2$, which exceed current densities available from thermionic cathodes. Emission from gated FED's can be initiated by the application of gate voltages of less than 100 V.

Driver circuitry, similar to that of field emission displays permits one or a number of tips of to be individually addressed so as to direct an electron beam 32 through the vacuum towards anode 30 which will cause the emission of X-rays at a small localized area on the face of X-ray source 20. As many thousands of electron tips, set forth in a row by column array 22 are individually addressable by the driver circuitry, emission of X-rays from device 20 can follow a raster scan pattern, similar to that of displays, or one or more tips can be addressed on a pixel by pixel basis.

FEDs with intense electron beams and short pulse durations provide the basis for a scanned X-rays source when anode 30 is a thin metallic film supported by an X-ray transparent beryllium window 34. Regular X-ray tubes emit photons with a broad range of energies, rather than at one or more discrete energies and they are emitted in a wide angle X-ray with monochromatic and quasi-collimated properties would improve the imaging significantly. Such thin film anodes can be provided by depositing a thin film of the X-ray generating material (such as molybdenum or rhenium or other material that provides characteristic emission in the forward direction) on a thicker sheet of X-ray transparent material (such as beryllium or amorphous carbon)

By adjustment and control of the parameters of electron beam 32 (its size, voltage and amperage) and the anode material 30 (composition and thickness) the pattern of the emitted X-rays can be controlled. For imaging applications an X-ray pattern that has an elongated forward projecting main lobe is preferred (illustrated as reference number 36 in FIG. 1) such a pattern will form a quasi-collimated X-ray beam in contrast to a broader non-collimated beam 38. A quasi-collimated X-ray beam can eliminate the need for external collimators located at either the X-ray source or the imaging device. Such external collimators operate by absorbing X-rays and their elimination will improve the efficiency of the system and thus reduce the dosage of X-rays needed to produce an image. Generally speaking, enhanced quasi-collimated characteristic fluorescence can dominate the X-rays when the thickness of anode 30 is in the order of 100 nm to 20 µm, depending on the specific element forming the anode. For example, for Mo—K$_\alpha$ we expect this thickness to be of the order of 10 µm or less.

Also, the use of hybrid-emission material whereby, in effect, dual or multiple energy emission can be generated on a pixel-by pixel basis. The addressing scheme can provide for both binary and grey-level energy spectrum selection of X-ray target material within a given sensor pixel. This is because, with modern fabrication technology, it is possible to have several emission electrode surfaces within a single detection pixel. For example, the anode need not be a single layer of material, rather it can be a multilayered structure of materials having differing X-ray emission properties or a laterally patterned structure with multiple materials (within each emission pixel).

The X-ray Detector

The current FDA-approved digital medical imaging systems are based on amorphous silicon transistor array and photodiodes coupled to an X-ray scintillator. The scintillator is based on crystalline pillars of cesium iodide (CsI). The X-ray detector of the present invention is based on a phosphor filled microchannel scintillator technology which achieves a contrast modulation that exceeds that of CsI scintillators.

Figure 2:
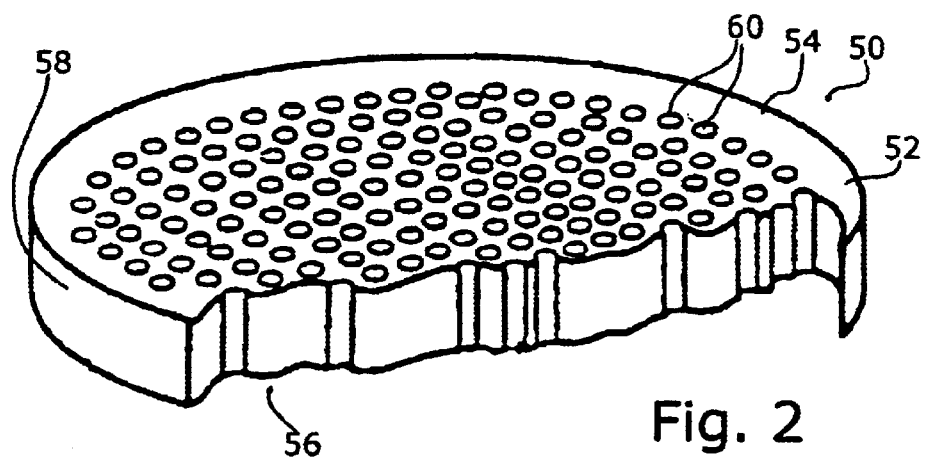
FIG. 2 is a perspective view of a phosphor filled microchannel plate used to detect the emitted X-rays.

FIG. 2 illustrates a composite phosphor screen 50 for converting radiation impinging thereon to visible light which has particular use in an X-ray imaging system. Phosphor screen 50 comprises a substrate 52 which has an upper planar surface 54, a lower planar surface 56 and a cylindrical edge 58. Etched from upper surface 54 to lower surface 56 of substrate 52 are a multiplicity of extremely small channels ("microchannels") 60 which have a width on the order of 0.05–50 µm (microns) and which are filled with phosphors that emit visible light when exposed to X-rays. The walls of microchannels 60 have a reflective coating to reflect the light down microchannels 60 towards an imaging device, this arrangement provides optical confinement of the light within the microchannel. The material used as the substrate is not critical: it can be glass, plastic, silicon as well as metals such as aluminum as techniques for the micro formation of microchannels exist for all of these materials. Furthermore, substrate 52 need not be circular in plan view, as it can be of any configuration and larger sizes can be made from a number of substrates tiled together. A pixelated CCD or CMOS imaging sensor may be readily attached to the back surface of screen 50. In this arrangement one or more microchannels will act on each pixel of the imaging sensor. As such X-rays impinging on a small part of screen 50 will cause light to be emitted from the microchannels located at the area of X-ray impingement the light will be transmitted down the microchannels to the corresponding pixels of the imaging sensor.

The Active-Synchronized Imaging System

Figure 3:
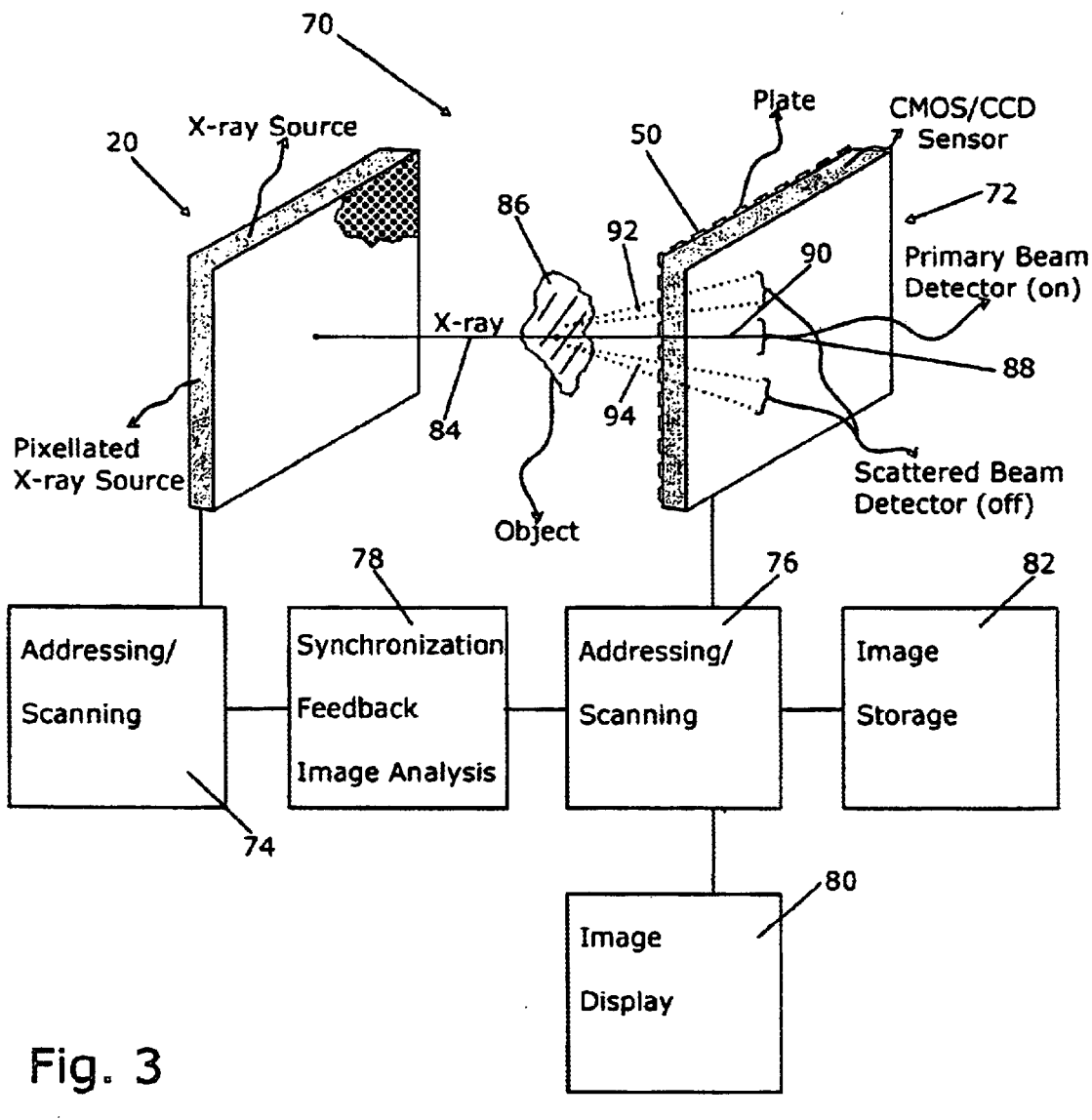
FIG. 3 is a schematic view of the X-ray imaging system of the present invention.

FIG. 3 illustrates schematically an X-ray imaging system 70 constructed in accordance with the present invention. Imaging system 70 includes the pixelated addressable field effect X-ray source 20 and the pixelated microchannel X-ray screen 50, both of which are described above, together with a CCD or CMOS pixelated imaging sensor 72 coupled to X-ray screen 50. X-ray source 20 is operated by scanning/addressing circuitry 74 which permits only certain pixels of source 20 to be activated or to cause a scanned source of X-rays to be provided. Imaging sensor 72 is connected to its scanning/addressing circuitry 76 which permits only certain pixels of sensor 72 to be read out. Synchronization circuit 78 is connected to addressing circuits 72, 74 so as to permit corresponding pixels of X-ray source 20 and sensor 72 to operated synchronously without the other pixels being active. Imaging sensor 72 is also coupled to a conventional image display 80 and storage system 82 which may be implemented by the display and storage hardware of a conventional personal computer.

In operation circuit 74 will operate to cause a scanned narrow X-ray 84 beam to emanate from X-ray source 20 which will pass through the object 86 to be examined. Simultaneously circuits 76, 78 will activate only the pixel 88 on sensor 72 that corresponds to the primary beam 90 that passed through object 86, scattered beams 92, 94 emanating from object 86 will not be detected by sensor 72 as the pixels on which scattered beams impinge are not activated. As the X-ray generating pixels of X-ray source 20 are operated in a scanned manner synchronously with the corresponding pixels of sensor 72 an X-ray image of object 86 will be generated without being effected by beam scattering, A key element of the present invention is the synchronizing of emission and detection, as well as active scanning as implemented by the feedback and image analysis circuitry of block 78. By selectively turning on "narrow" emitters and detectors, only highly correlated signals are recorded. Scattered radiation is not detected. This is superior to allowing only the sensing of collimated X-rays with grids. Since, in the active pixel/emitter case with a quasi-collimated beam, all the radiation contributes to the final image. Whereas in the "grid" or "aperture" approach, only some of the incident X-rays contribute to the final image. In the limit, if only one emission pixel and one detector pixel were simultaneously energized, no scatter from the body will be allowed.

Another important component of the present invention is the concept of "active"sub-frame exposure. Current imaging systems expose the entire sensing area to a nearly uniform flood of X-rays. The mean density of the object and the desired contrast detectability determines the actual exposure. By design, some areas receive unnecessary amount of X-ray photons, while another receives the bare minimum for adequate contrast or high frequency resolution. Sub-frame optimal exposure, on the other hand, can monitor the S/N of each pixel and in CT mode, each voxel. Each pixel can then be automatically adjusted by the control circuitry to receive only the flux necessary to ensure adequate discrimination. The present thus provides automatic feature detection and extraction. The system can be used to "fill-in" or optimally expose only those areas that are problematic. This would not be possible with a mechanically scanned system relying on a single, expanding beam.

Alternative Embodiments

Figure 4A:
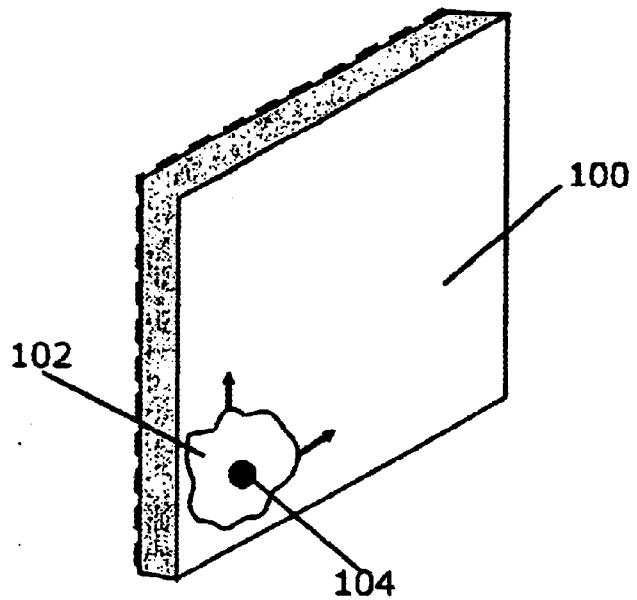
FIG. 4a is a perspective view of the X-ray detector, that has been partially cut away to show an X-ray blocking screen having an aperture disposed therein.
Figure 4B:
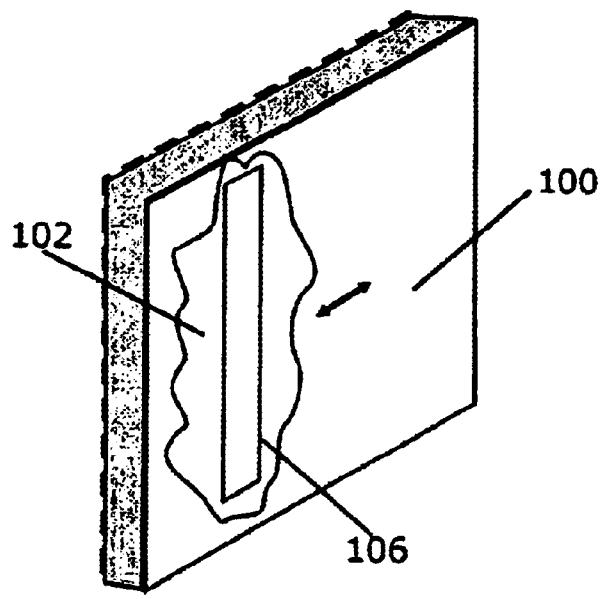
FIG. 4b is a perspective view of the X-ray detector, that has been partially cut away to show an X-ray blocking screen having a slot disposed therein.

FIGS. 4a and 4b illustrate an embodiment of the present invention in which the pixelated addressable X-ray detector described above is replaced with a non addressable detector while retaining scatter free. In FIG. 4a a standard non-pixelated, non addressable phosphor screen 100 is used, disposed in front of screen 100 is an X-ray blocking screen 102 which is moveable in the X and Y directions (as shown by the arrows). Disposed in screen 102 is an aperture 104 through which X-rays may pass to impinge on phosphor screen 100. X-ray blocking screen is preferably driven by electric motors under the control of addressing/scanning circuitry 78 such that the movement of aperture 104 is synchronized and corresponds in spatial position with the portion of X-ray source 20 that is emitting X-rays. Thus, only a portion of X-ray detecting screen is "active" at any one time. FIG. 4b is similar to that of FIG. 4a except that the X-ray admitting aperture 104 is replaced by an X-ray admitting slot 106 which is translatable in a single direction across phosphor screen 100.

In addition to the phosphor screens described above the present invention may utilize "storage phosphor" imaging screens, such as those described in U.S. patent application Ser. No. 10/073,702 filed Feb. 11, 2002 Entitled "High Resolution Tiled Microchannel Storage Phosphor Based Radiation Sensor" which has been incorporated by reference herein. The X-ray photons forming the image of patient or object are absorbed by an storage phosphor imaging screen which will store a dose proportional amount of energy corresponding to a latent image for an indefinite period of time. At a later time and perhaps at a different location, a focused Helium-Neon (He—Ne) laser is raster scanned across the back of storage phosphor imaging screen to read out the latent image. The red light of He—Ne laser stimulates recombination resulting in photostimulated luminescence whose intensity is proportional to the X-ray dose. For each spot of imaging screen the intensity of the photostimulated luminescence is measured by a Photomultiplier tube and can be stored in a control computer. The image can be visualized by a monitor screen or a hard copy output. Thermal means can also be used to read out the image by thermally stimulated luminescence.

The use of storage phosphor imaging screens provide flexibility in use as they may be removed from the imaging device and read at a different place and time from the imaging exposure. Furthermore, the imaging plates can be read out from either the front or rear surface of the imaging screen. The high resolution provided by the use of microchannel imaging plates such as that shown in FIG. 2 herein will not be lost, as standard storage phosphors, such as barium flourobromide (BaFBr:Eu$^{2+}$) doped with europium 2$^+$, can readily be obtained in sizes sufficient to be disposed in the microchannels. When a microchannel plate is read out from the front side, rather than from the back side, a number of design parameters of the microchannel plate are eased. The plate can be thicker, and thus easier to handle as only the phosphors in the upper portion of the plate are read out to form the image. In plates that are read from the back, thick plates mean relatively long microchannels which, because of the many internal reflections of the light that occur, can adversely affect light output with backside readout. The fact that only the phosphors in the upper portion of the microchannels are read also means that the microchannel need not be filled all the way down and the lower potion of the filled with non light emitting material. Furthermore, in a front read microchannel plate, the microchannels need also not be uniformly plated with a highly reflective coating all the way down the microchannels.

While the above description has emphasized medical imaging applications it is to be noted that the benefits of the present invention are equally applicable to industrial X-ray imaging application. The present invention has been described with respect to exemplary embodiments. However, as those skilled in the art will recognize, modifications and variations in the specific details which have been described and illustrated may be resorted to without departing from the spirit and scope of the invention as defined in the appended claims.

What is claimed is:

1. An X-ray system for examining an object comprising:
  a source of X-rays operated such that the X-rays are emitted from only a portion of the surface of the X-ray source;
  an X-ray detector having means such that only a portion of the X-ray detector is active at any one time;
  means for synchronizing the X-ray source and X-ray detector such that a corresponding area of the X-ray detector is activated when the corresponding area of the X-ray source is emitting X-rays; and
  feedback means for monitoring the X-ray flux received by each of the individual X-ray detecting portions of the X-ray detector; and controlling the amount of flux received by each of the active portions in response to the monitored X-ray flux.

2. The X-ray system as claimed in claim 1 wherein the X-ray source comprises a plurality of X-ray emitting pixels, with only certain ones of the pixels activated at any one time.

3. The X-ray system as claimed in claim 1 wherein the means for activating a portion of the X-ray detector comprise electronic means.

4. The X-ray system as claimed in claim 1 wherein the means for activating a portion of the X-ray detector comprise an aperture movable across the surface of the X-ray detector.

5. The X-ray system as claimed in claim 1 wherein the means for activating a portion of the X-ray detector comprise a slot translatable across the surface of the X-ray detector.

6. The X-ray system as claimed in claim 1 wherein the X-ray detector includes a plate having a plurality of microchannels disposed therein with phosphors disposed in said microchannels.

7. The X-ray system as claimed in claim 1 wherein the X-ray detector includes storage phosphors.

8. The X-ray system as claimed in claim 1 wherein the X-ray source comprises a field emission device.

9. The X-ray system as claimed in claim 1 wherein the individually addressable X-ray emitting portions of the X-ray source comprise at least one cathode tip directing a beam of electrons towards an X-ray emitting anode.

10. The X-ray system as claimed in claim 1 wherein the X-ray source comprises a multiplicity of small cathode tips directing a beam of electrons towards an X-ray emitting anode.

11. An X-ray system for examining an object comprising:
  an X-ray source comprising individually addressable X-rays emitting portions;
  means for activating the individual X-rays emitting portions in a predetermined sequence an X-ray detector comprising individually addressable X-rays detecting portions;
  means for activating the individual X-rays detecting portions in a predetermined sequence,
  means for synchronizing the X-ray source activating means and X-ray detector activating means such that a corresponding portion of the X-ray detector is activated when the corresponding portion of the X-ray source is emitting X-rays;
  means for monitoring the X-ray flux received by each of the individual X-rays detecting portions of the X-ray detector; and
  means for controlling the amount of flux received by each of the individual X-rays detecting portions in response to the monitored X-ray flux.

12. The X-ray system as claimed in claim 11 wherein the X-ray source comprises a field emission device.

13. The X-ray system as claimed in claim 11 wherein the individually addressable X-ray emitting portions of the X-ray source comprise at least one cathode tip directing a beam of electrons towards an X-ray emitting anode.

14. The X-ray system as claimed in claim 11 wherein the X-ray detector includes a plate having a plurality of microchannels disposed therein with visible light emitting phosphors disposed in said microchannels.

15. The X-ray system as claimed in claim 11 wherein the X-ray detector comprises a multiplicity of individually addressable pixels.

16. The X-ray system as claimed in claim 11 wherein the X-ray source comprises a multiplicity of small cathode tips directing a beam of electrons towards an X-ray emitting anode.

17. The X-ray system as claimed in claim 11 further including an image storage and image display system.

18. An X-ray system for examining an object comprising:
  an X-ray source comprising individually electronically addressable X-ray emitting pixels;
  electronic means for addressing the individual X-rays emitting pixels in a predetermined sequence
  an X-ray detector comprising electronically individually addressable X-ray detecting pixels;
  means for addressing the individual X-rays detecting pixels in a predetermined sequence,
  electronic means for synchronizing the X-ray source addressing means and X-ray detector addressing means such that a corresponding portion of the X-ray detector is activated when the corresponding portion of the X-ray source is emitting X-rays, said electronic means including means for adjusting the exposure of the X-rays detecting pixels in accordance with the amount of X-rays impinging thereon.

19. The X-ray system as claimed in claim 18 wherein the X-ray detector includes a plate having a plurality of microchannels disposed therein with visible light emitting phosphors disposed in said microchannels.

20. The X-ray system as claimed in claim 18 wherein the X-ray source comprises a multiplicity of field emission devices disposed in an array.

* * * * *